United States Patent [19]

Bergelson et al.

[11] Patent Number: 5,467,773
[45] Date of Patent: Nov. 21, 1995

[54] CARDIAC PATIENT REMOTE MONITORING USING MULTIPLE TONE FREQUENCIES FROM CENTRAL STATION TO CONTROL FUNCTIONS OF LOCAL INSTRUMENT AT PATIENT'S HOME

[75] Inventors: Michael N. Bergelson, Riverdale, N.Y.; Nartzis Naydenov, Hackensack, N.J.

[73] Assignee: Paceart Associates, L.P., Wayne, N.J.

[21] Appl. No.: 65,669

[22] Filed: May 21, 1993

[51] Int. Cl.[6] .................................................. A61B 5/02
[52] U.S. Cl. .................... 128/709; 128/695 R; 128/904; 379/102
[58] Field of Search .................................. 128/904, 695, 128/696, 700, 702; 379/102–106

[56] References Cited

U.S. PATENT DOCUMENTS 4,095,050  6/1978  Beachem et al. ...................... 379/102
4,596,900  6/1986  Jackson .................................. 379/102
4,838,275  6/1989  Lee ........................................ 128/904

Primary Examiner—William E. Kamm
Assistant Examiner—Marianne Parker
Attorney, Agent, or Firm—Cooper & Dunham

[57] ABSTRACT

Remote monitoring of cardiac electrical activity and/or pacemaker function under extensive control by personnel at a central station over the operation of a monitoring instrument at the patient's home, to thereby reduce reliance on active participation by the patient and to enhance useful information and suppress undesirable information in the signals transmitted between the home monitoring unit and the central station.

14 Claims, 5 Drawing Sheets

CARDIAC PATIENT REMOTE MONITORING USING MULTIPLE TONE FREQUENCIES FROM CENTRAL STATION TO CONTROL FUNCTIONS OF LOCAL INSTRUMENT AT PATIENT'S HOME

FIELD OF THE INVENTION

The invention is in the field of monitoring a patient's electrical cardiac activity and pacemaker operation from a central station via a telephone connection.

BACKGROUND OF THE INVENTION

Cardiac patients can have their cardiac activity monitored from a central location via a telephone connection while they remain at home. Such monitoring is particularly useful for patients with implanted heart pacemakers and/or certain heart conditions such as symptomatic arrhythmia episodes. Typically, the patient dials the telephone number of a central monitoring station from a home telephone set, or the center dials the patient's telephone number, to establish a two-way telephone connection over the public telephone switching network. A person at the central station then guides the patient through the steps needed to set up the system for remote monitoring and, when satisfied, asks the patient to place the telephone handset on an acoustic coupler at the home monitoring instrument. A microphone in this coupler is driven by electrical signals supplied to the home instrument over ECG electrode leads, and the sound produced by this speaker in turn drives the telephone handset's microphone which converts it to an electrical analog signal. This analog signal is encoded at the home instrument and sent over the telephone line to the central station for assessment. From time to time, the person at the central station alerts the patient via an alert signal to take some other action. This alert signal may be generated by pushing a number key at the dialing keypad of the dual tone multifrequency telephone set in the central station, and can be used to turn on an indicator light and/or to sound an alarm at the patient's home telephone set.

While such remote monitoring through a home instrument has been useful, it is believed that existing systems still have disadvantages such as critical reliance on the patient to take certain actions in a timely and accurate manner and possible distortion of the data due to interaction in the transmitted signal of pacemaker pulses superimposed on the cardiac electrical activity signal. Inappropriate action on the part of the patient can be a significant problem in this field in view of the age group of the patients that typically use home telephone monitoring of heart and pacemaker function.

An improvement which is believed to improve reliability in some respects is discussed in U.S. Pat. No. 4,938,229 which shares a co-inventor with this application and is hereby incorporated by reference. This improvement has been used for more than a year in this country by the assignee of this invention for remote monitoring of heart and pacemaker function via telephone. U.S. Pat. No. 4,938,229 discusses techniques for encoding ECG and pacemaker data into an FM signal and transmitting the so-encoded data to a central monitoring station for assessment by health care personnel. In addition, other companies are believed to have been involved in supplying equipment for monitoring of heart and pacemaker functions over the telephone. They include Instrumedix in Beaverton, Oreg., Norland Corporation in Fort Atkinson, Wis., Medtronic, Inc. of Minneapolis, Minn., and possibly others.

SUMMARY OF THE INVENTION

An object of the invention is to improve home monitoring of heart patients via the telephone network by providing a more convenient and reliable system and method for such monitoring and by overcoming at least some of the disadvantages of existing monitoring systems.

In accordance with one aspect of the invention, remote monitoring of cardiac electrical activity and/or pacemaker function is improved by providing greater control by personnel at the central station over the operation of the monitoring instrument at the patient's home, to thereby reduce reliance on active participation by the patient, and by providing a greater ability to enhance useful information and suppress undesirable information in the signals transmitted between the home monitoring unit and the central station.

In a non-limiting example, the invention is embodied in an integrated instrument that typically is in the patient's home and combines, in a single unit, a modified home telephone set and a special home patient monitoring device. The home instrument communicates via the public telephone switching network with a remote instrument which is at a central monitoring station attended by health personnel. The instrument at the central station includes a dual tone multifrequency telephone set as well as equipment for assessing ECG and pacemaker data received from the patient's home and typically further includes equipment for maintaining and using a database of patient records.

The modified telephone set circuitry in the home instrument includes the normal parts of a dual tone multifrequency telephone that serve to establish a two-way speaking connection between the home instrument and the instrument at the central monitoring station, such as the normal telephone control circuitry, a dual tone multifrequency dialing keypad, and a microphone and a speaker in the handset and, optionally a speaker and a microphone in the base unit to allow hands-free operation. In accordance with the invention, this telephone circuitry is modified by the addition of a DTMF (dual tone multifrequency) decoder chip coupled with the telephone line to decode DTMF signals received at the home instrument after the two-way communication with the central station has been established. This DTMF decoder converts received DTMF signals into local commands for turning on and off circuits in the monitoring part of the home instruments to ensure proper sequencing of operations without the need for active participation by the patient, and to provide alerts and messages to the patient. Still in addition, the telephone circuitry is modified by adding a microphone gate which receives the output of the telephone set's normal microphone(s) and further receives an encoded signal representing the output of the monitoring part of the home instrument.

The monitoring part of the home instrument receives cardiac electrical activity and pacemaker data from ECG leads, extracts any one of several types of information from the received data, converts the extracted information to a form that is particularly suitable for transmission over a telephone line, transmits the data through an isolation stage to the telephone part of the home instrument and therethrough to the central station, and responds to local commands decoded by the DTMF decoder to turn on and off selected circuits and to display messages and/or otherwise alert the patient.

To this end, the monitoring part of the home instrument comprises an input connector for ECG leads supplying cardiac electrical activity waveforms and any pacemaker pulses, and an amplifier coupled to the input connector to receive the input signals. The amplifier processes the cardiac electrical activity waveforms and any pacemaker pulses superimposed thereon and provides a composite analog output signal.

In accordance with the invention, the home instrument selectively operates in any one of three modes: (a) transmit to the central station only cardiac electrical activity waveforms (by stripping or suppressing any superimposed pacemaker pulses from the signal supplied from the ECG leads); (b) transmit the cardiac electrical activity waveforms and only the time of occurrence of pacemaker pulses but not the width of the pacemaker pulses; and (c) transmit each of the cardiac electrical activity waveforms, the time of occurrence of pacemaker pulses, and the duration of pacemaker pulses. In mode (a), the output of the amplifier passes through an ECG filter which suppresses any pacemaker pulses that may be superimposed on the cardiac electrical activity waveforms and transmits the filtered waveforms to an FM encoder which encodes them into an FM signal using techniques disclosed in said U.S. Pat. No. 4,938,229. In this mode (a), a logic control in the monitoring part of the home instrument makes sure that the FM encoder will receive and encode only signals from the ECG filter, so that only the encoded ECG filter output will be supplied to the isolation stage and will be transmitted to the central station. In mode (b), the logic control makes sure that the FM encoder will receive and encode both the output of the ECG filter and an output from a network that extracts pacemaker pulses from the signal delivered over the ECG leads and converts each to a pulse which has a fixed duration and amplitude to thereby signify only the time of occurrence, not the duration, of a respective pacemaker pulse. This network includes a pulse filter which receives the output of the same amplifier and suppresses the cardiac electrical activity waveform in order to pass only or mainly pacemaker pulses present in the amplifier output. The output of the pulse filter goes to a pulse detector which responds to each leading and each trailing edge of a pacemaker pulse to generate a respective short pulse. These short pulses in turn go to a pulse encoder (fixed) which, in response to each short pulse signifying a leading edge of a pacemaker pulse, outputs a pulse of a fixed duration and amplitude and delivers its output to the FM encoder. The FM encoder encodes each such fixed duration and amplitude pulse and delivers the resulting FM signal to the isolation stage for transmission to the central station along with the FM encoded cardiac electrical activity waveforms. Last, in mode (c) the short pulses from the pulse detector which signify the times of occurrence of the leading and trailing edges of pacemaker pulses go to a pulse width detector which, in response to each pair of such short pulses that come from a single pacemaker pulse, generates a pulse that is as wide as the pacemaker pulse but has a fixed amplitude. This fixed amplitude pulse goes to a pulse encoder (x33) which converts it to a pulse which has the same fixed amplitude but is 33 times as long (wide). The pulse encoder (x33) delivers this wide pulse to the FM encoder for conversion to a corresponding FM signal. In this mode (c), the logic control makes sure the FM encoder will receive and encode only the outputs of the ECG filter and of the pulse encoder (x33), not the output of the pulse encoder (fixed).

In addition, the monitoring part of the home instrument includes a patient alert indicator which generates a light and/or an audible signal to alert the patient to take some action when so signaled by the logic control, and further includes a power supply, such as a battery-powered supply, which can be turned on and off by the patient but can also be turned off by a signal from the logic control in response to a locally decoded DTMF signal from the central station, and a power indicator to show the condition of the power supply (the battery).

The logic control circuit controls the operation of the FM encoder, of the two pulse encoders, and of the patient alert indicator, and which turn off the power supply, in response to local commands which the DTMF decoder decodes from dual tone multifrequency signals received from the central station over the telephone line after a two-way telephone connection has been established.

A first alternative embodiment differs in that the monitoring part of the home instrument discussed above and the DTMF chip are built into the handset of a portable home telephone so that the normal RF communication between the handset and the base unit obviates the need for electrical isolation between the ECG electrodes and the telephone line of the type provided in the first embodiment by the isolation stage. In addition, in this second embodiment the normal wall outlet connection of the portable telephone can be used to power the telephone circuits housed in the base unit while the normal rechargeable battery in the handset can be used to power the remaining ones of the circuits discussed above. In a second alternative embodiment, the home instrument is separated into a telephone unit and a separately packaged monitoring unit, and an acoustic coupler is used between a speaker driven with the output of the FM encoder and the microphone of the telephone's handset. This again obviates the need for the isolation stage of the first embodiment.

The modified telephone part of the home instrument is electrically isolated from the heart monitoring part by an isolating stage which permits communication between them only via optical signals.

DETAILED DESCRIPTION

Figure 1:
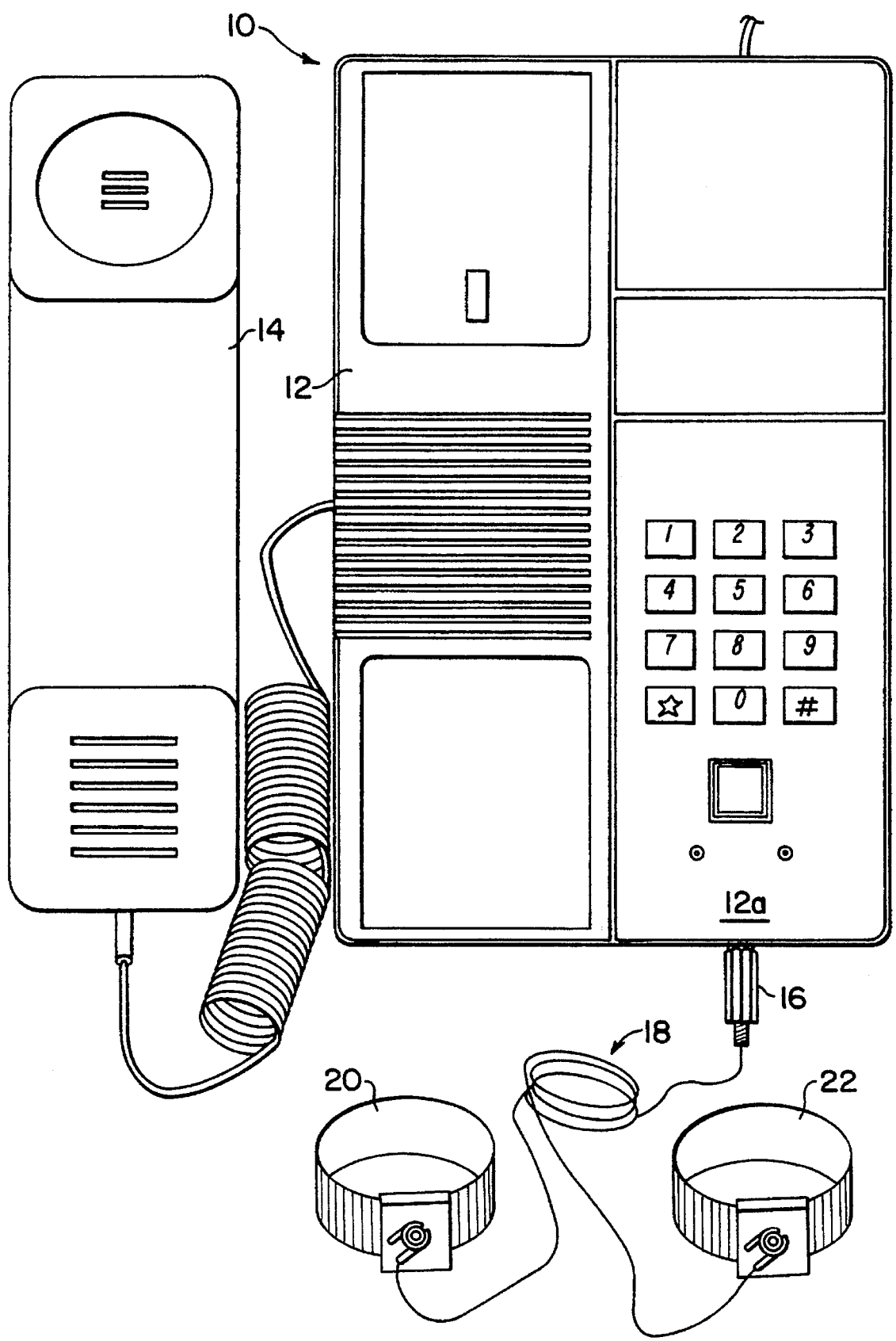
FIG. 1 is an illustration of a local instrument incorporating in one single unit a modified dual tone multifrequency telephone set and patient heart function monitoring circuits utilizing features of the invention.

Referring to FIG. 1, a home instrument 10 comprises a base unit 12 and a handset 14 and encloses in one single, integrated unit the circuitry of a conventional dual tone multifrequency telephone and certain modifying circuitry as well as special circuitry for monitoring cardiac electrical activity and pacemaker function and for transmitting and receiving data associated with such monitoring. Base 12 has an input 12a accepting a plug 16 of ECG leads 18 supplying signals from ECG electrodes such as wrist electrodes 20 and 22. While only two wrist electrodes are illustrated, it should be clear that the invention is equally useful with disposable ECG electrodes, or with 12-lead electrodes, or with electrodes coupled with other parts of the body, or with a different number or type of ECG electrodes.

Figure 2:
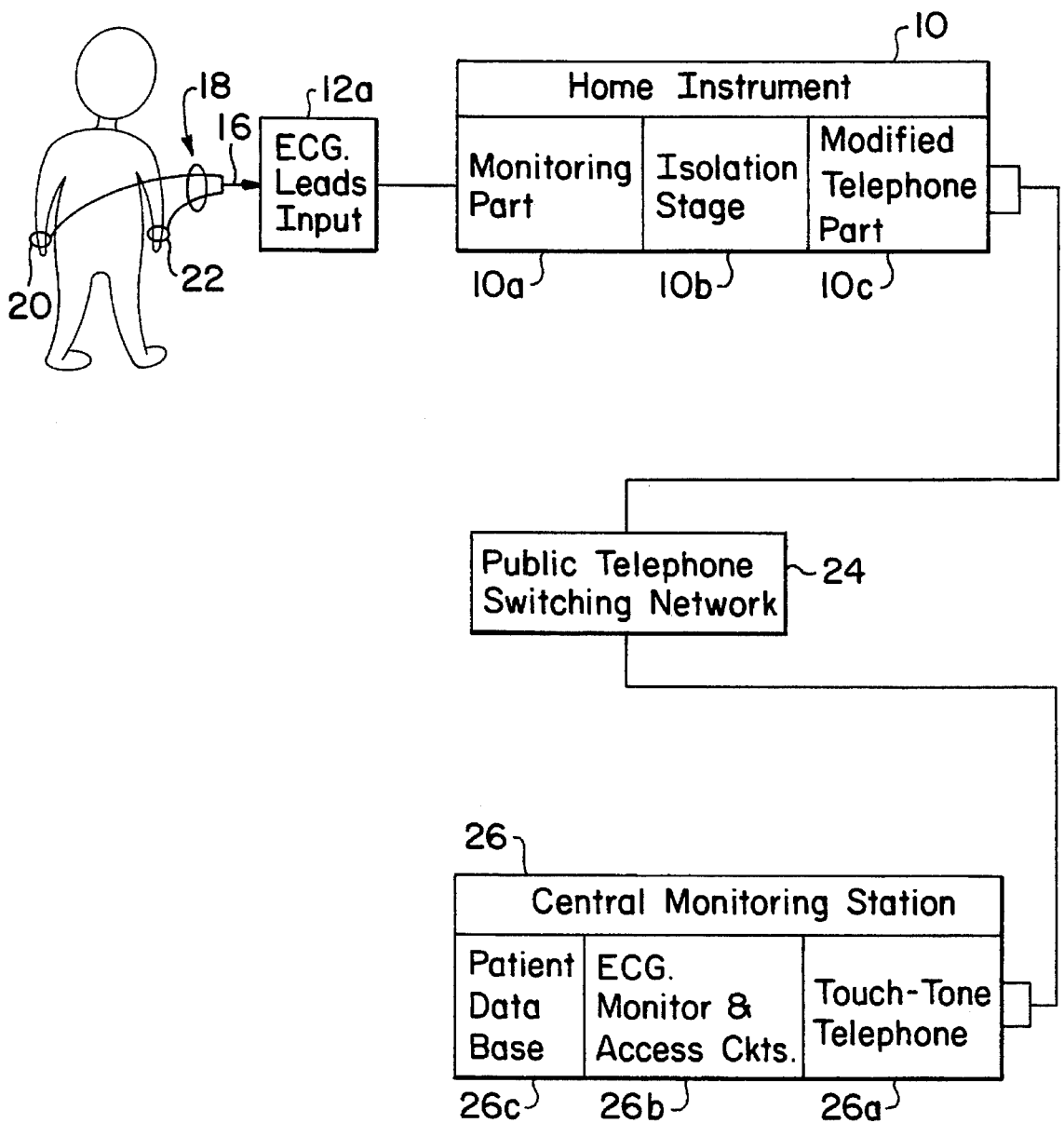
FIG. 2 is an overall block diagram illustrating a connection of the local instrument with a central heart function monitoring station via the public telephone switching network.

As illustrated in FIG. 2, home instrument 10 includes a monitoring part 10a connected with ECG leads input 12 to receive therefrom the signals supplied through plug 16 and ECG leads 18 from ECG electrodes such as wrist electrodes 20 and 22. Monitoring part processes these signals and supplies a processed output, through an isolation stage 10b, to a modified telephone part 10c. Home instrument 10 connects through public telephone switching network 24 with a central monitoring station 26 which includes a dual tone multifrequency telephone set 26a, ECG monitoring and assessing circuits 26b and, optionally, patient data base 26c.

Figure 3:
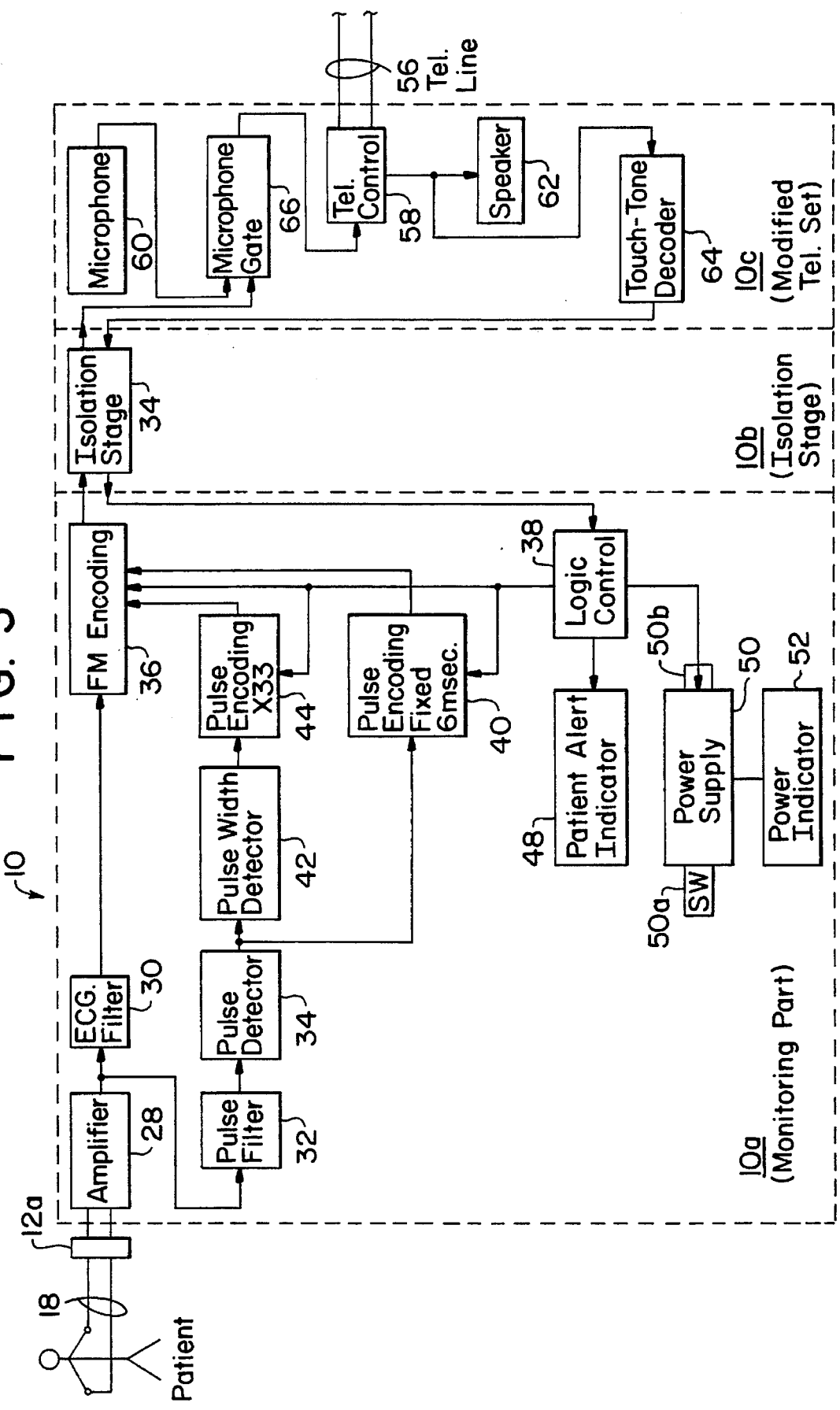
FIG. 3 is a more detailed block diagram of the local instrument which typically is at the patient's home.

Referring to FIG. 3, the monitoring part 10a of home instrument 10 receives cardiac electrical activity waveforms and any pacemaker pulses superimposed thereon from ECG leads 18 at input 12a, and supplies the received analog signals to the inputs of an amplifier 28 which can be a conventional two-input differential amplifier of the type used in monitoring units of this general type. An additional ground lead (not shown), connected to an electrode at the patient's leg, can supply ground reference to a ground input of amplifier 28. Of course, if 12-lead ECG electrodes are used, or if the number of ECG electrodes is different, a suitably modified amplifier will be used as is known in the pertinent technology. Amplifier 28 supplies its output to each of an ECG filter 30 and a pulse filter 32. The signal path through ECG filter 30 pertains to processing cardiac electrical activity signals while that through pulse filter 32 pertains to processing pacemaker pulses. ECG filter is a low pass filter which suppresses the rapid signal amplitude changes which characterize pacemaker pulses but passes the more gradual amplitude changes that characterize cardiac electrical activity (qrst) waveforms. In contrast, pulse filter 32 is a high pass filter which passes the sharp leading and trailing edges of pacemaker pulses but suppresses the more gradual amplitude changes of the QRS waveforms. For example, ECG filter can have a bandpass of 0.5 Hz to 40 Hz while pulse filter 32 can have a bandpass of 100 Hz to 10–15 KHz, or can be a 15 KHz notch filter. The pacemaker pulses that pass through pulse filter 32 go to a pulse detector 34 which identifies and encodes the leading and trailing edges of the pacemaker pulses. Pulse detector 34 can be a conventional edge detector circuit which responds to rising and falling edges of a pulse to output, for each edge, a respective short pulse that has a fixed duration and a fixed amplitude. Typically, a pacemaker pulse varies in width from about 0.2 msec to about 2 msec. In response to each edge of such a pulse, pulse detector 34 outputs a pulse of a fixed amplitude and a duration fixed at about 0.05 msec.

In a first mode of operation, home instrument 10 transmits only information regarding cardiac electrical activity waveforms, not about pacemaker pulses. In this first mode, the output of ECG filter 30 goes to an FM encoder 36 which encodes its time-varying amplitude into an FM signal, using techniques disclosed in said U.S. Pat. No. 4,938,229. In this first mode, a logic control circuit 38 inhibits other signals that can be supplied for encoding at FM encoder 36 as described below.

In a second mode, monitoring part 10a transmits two types of information to isolation stage 10b: the cardiac electrical activity waveforms and the time of occurrence of pacemaker pulses. However, it does not transmit information regarding the width of the pacemaker pulses. Logic control circuit 38 in this mode inhibits other signals that can be supplied to FM encoder 36 as described below. In this second mode, the short pulses of fixed amplitude into which pulse encoder 34 encodes each leading and trailing edge of each pacemaker pulse go to a pulse encoding (fixed) circuit 40 which encodes each pair of successive short pulses from pulse detector 34, which signify the leading and trailing edges of a pacemaker pulse, into a single pulse of a fixed duration (e.g., 6 msec) and a selected amplitude. Pulse encoder (fixed) 40 sends each such 6 msec pulse to FM encoder 36 for encoding into an FM signal. Thus, in this second mode FM encoder receives information both regarding the cardiac electrical activity and the pacemaker electrical activity (the time of occurrence of pacemaker pulses), forms a composite FM signal that contains information regarding both processes and delivers this composite FM signal to isolation stage 10b.

In a third mode of operation, monitoring part 10a encodes into an FM signal each of: (i) the cardiac electrical activity waveforms; (ii) the time of occurrence of pacemaker pulses; and (iii) the duration of pacemaker pulses. In this third-mode, the short pulses from pulse detector 34 which signify the leading and trailing edges of pacemaker pulses are additionally processed in a pulse width detector 42 which, in response to each pair of such short pulses that come from a single pacemaker pulse, generates a pulse that is as wide as the pacemaker pulse but has a selected amplitude. This selected amplitude pulse goes to a pulse encoder (x33) 44 which converts it to a pulse which has a corresponding selected amplitude but is 33 times as long (wide). Pulse encoder (x33) 44 delivers this wide pulse to FM encoder 36 for conversion to a corresponding FM signal. In this third mode, logic control circuit 38 makes sure FM encoder will receive and encode the output of each of ECG filter 30, of pulse encoder (x33) 44, and of pulse encoder (fixed) 40 into a single composite FM signal for delivery to isolation stage 10b.

In addition, monitoring part 10a includes a patient alert indicator 48 which generates a light and/or an audible signal to alert the patient to take some action when so signaled by logic control circuit 38. In a specific example of the invention, patient alert indicator 48 can be an LED display which, when turned on by a signal from logic control 38, alerts the patient to the fact that he or she should speak with the person at central station 26 over the telephone. A power supply 50 in monitoring part 10a can be a battery-powered supply that includes a switching circuit which can be turned on and off though a manual switch 50a by the patient but can alternatively be turned off by a signal sent to switch 50b from logic control circuit 38 in response to a locally decoded DTMF signal from the central station as described below. Still in addition, monitoring part 10a includes a power indicator circuit 52 coupled with power supply 50, which can be an LED indicator that lights up when power supply 50 is on. For clarity, the power supply connection from power supply 50 to the other circuits in FIG. 3 are not shown.

Isolation stage 10b includes a single circuit in the form of an optical isolation stage 54 which converts electrical signals received from each side (monitoring part 10a and modified telephone set 10c) into respective optical signals and delivers the optical signals to an optical receiver which converts them back to electrical signals for delivery to the other side (telephone set 10c and monitoring part 10a, respectively). Isolation circuit 54 thus provides electrical isolation between the telephone network and the patient side of home instrument 10.

Modified telephone set 10c comprises the normal telephone circuitry found in most home touch telephone sets, including a suitable connector to a telephone line 56, a telephone control circuit 58, microphone 60 and speaker 62. Telephone control circuit 58 operates as in a normal home telephone set to detect and respond to ring and tip signals, to amplify speech generated signals, to produce dial tone, etc. Microphone 60 and speaker 62 can be the normal units contained in the handset. Alternatively, a microphone and a speaker and the associated circuitry can be included in the base unit to allow for hands-free two-way telephone conversation.

Set 10c has been modified by the inclusion of a dual tone multifrequency decoder circuit 64 which can be a commercially available DTMF decoder chip operating in accordance with the public telephone switching network standards in this country to decode dialing frequency signals sent from central station 26 AFTER two-way communication with home instrument 10 has been established. When a person at central station 26 pushes a button on the dialing keypad of the dual tone multifrequency telephone there WHILE home instrument 10 and central station 26 have a two-way telephone speech connection, the dialing tone frequency signal that normally is used to dial a telephone number is transmitted via the telephone line to telephone control circuit 58 in home instrument 10, and is routed from there to dual tone multifrequency decoder 64.

In response to each different dialing frequency signal received thereby, dual tone multifrequency decoder outputs a respective unique binary code signal delivered to isolation stage 54 and, from there, to logic control 38. In response to these unique binary code signals, logic control 38 in turn controls the operation of circuits 36, 40, 48 and 50 through suitable logic gating. In addition, telephone set 10c has been modified by including a microphone gate 66 which responds to the presence of an FM encoded signal provided by FM encoder 36 to disconnect microphone 60 from telephone control 58 and thus avoid possible distortion of the FM encoded signal with noise from microphone 60.

Figure 4:
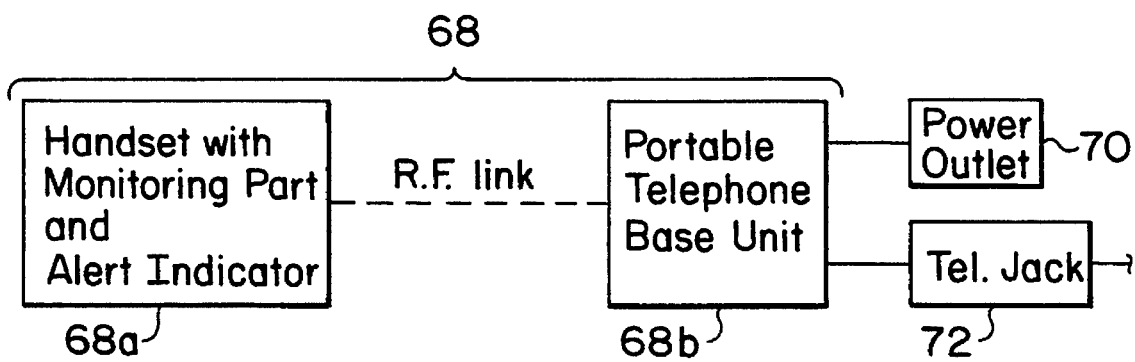
FIG. 4 illustrates an alternative embodiment using a portable home telephone with built-in modifications to carry out the invention.

A first alternative embodiment is illustrated in FIG. 4 and differs from that described above only in that monitoring part 10a of home instrument 10 discussed above and DTMF chip 64 are built into a handset 68a of a portable home telephone set 68 so that the normal RF communication between handset 68a and base unit 68b obviates the need for an isolation circuit 54 to provide electrical isolation between the ECG electrodes and the telephone line. In addition, in this second embodiment the normal wall outlet connection of portable telephone can be used to power the telephone circuits housed in base unit 68b from a wall power outlet while the normal rechargeable battery (not shown) in handset 68a can be used to power the remaining ones of the circuits discussed above. This modified portable telephone set in the patient's home is connected through a telephone jack 72 to the public telephone switching network and, therethrough, to central station 26.

Figure 5:
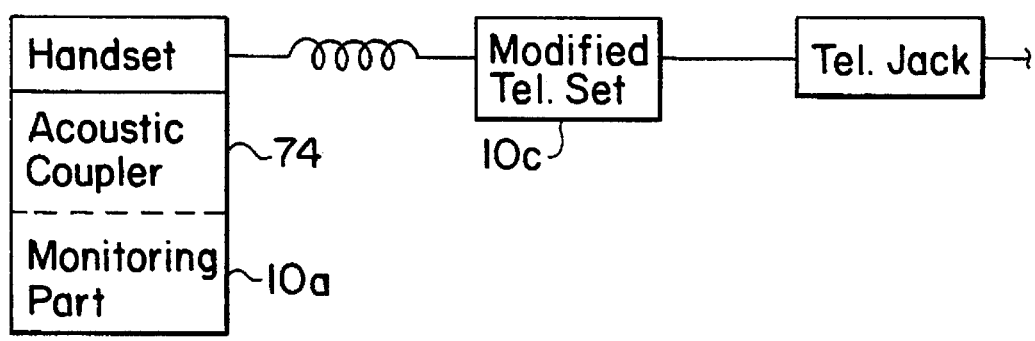
FIG. 5 illustrates another alternative embodiment using acoustic coupling between a home monitoring unit and a modified telephone set.

In a second alternative embodiment, illustrated in FIG. 5, home instrument 10 is separated into a modified telephone unit 10c and a separately packaged monitoring unit 10a which can be substantially the same electrically as the similarly numbered units illustrated in FIG. 3. However, instead of using an isolation stage 54, an acoustic coupler 74 is used to convert the FM encoded signal from monitoring part 10a into an acoustic signal that is acoustically coupled with handset 10c′ of set 10c. Of course, in this case microphone gate 66 in set 10c is not used.

In typical operation, the patient dials central station 26 or a person at central station 26 dials home instrument 10. Once a two-way speaking connection is established, the patient and the person at the central station converse until the central station is satisfied that monitoring can proceed, e.g., that the patient has turned on power supply 50 by manual operation of switch 50a, that the ECG electrodes 20, 22 are properly placed, that leads 18 and plug 16 are correctly connected to home instrument 10, and that the patient has available nearby a magnet for controlling a pacemaker (if needed), and that the patient and home instrument 10 are otherwise ready. The person at central station 26 can make certain preliminary tests at this time, by pushing buttons on the dialing keypad of the telephone at central station 26. The resulting signals are decoded by DTMF decoder 64 in home instrument 10 into local commands as illustrated in Table I below:

TABLE I

| Touch-Tone Key | Function |
|---|---|
| | Functions of Touch-Tone Keys for Controlling Phone |
| 2, 3 | Not Used |
| 1!-4 | Transmit ECG and measured pacemaker pulse duration (and marker indicating time of occurrence). |
| 1!-5 | Transmit ECG and marker indicating time of occurrence of pacemaker pulse. |
| 1!-6 | Transmit ECG ONLY. |
| 1!-0 | Turn transmitter off, to be used at end of session. |
| 8,9 | Not Used |
| 1!-7 | Patient alert. Lights red light on patient telephone, sounds audible tone, and permits operator to speak to patient. |

NOTE:
The symbol "N!" (where "N" is touch-tone key "N") indicates that the "N" key is to be held depressed for at least 3 seconds.

Using the dialing keypad, the person at central station 26 can carry out the following preliminary tests:

1. Press "1!-6" and ensure that a good ECG is being received. If not, alert the patient and ask the patient to move the electrodes.

2. Press "1!-5" to detect pacemaker pulses, and observe the pulses on the strip.

4. Press "1!-4" and ensure that pacemaker pulse widths are being measured.

5. Press "1!-7" to alert the patient, and repeat the instructions.

When the person at central station 26 is satisfied that all necessary preparations have been completed, actual monitoring can be carried out, for example by using the sequence illustrated in TABLE II below:

TABLE II

Typical Sequence for Monitoring Call Codes to be used with Touch-Tone Telephone at Center

| Step | Center Operation | Patient Operation |
|---|---|---|
| 1. | Dial patient | Patient answers. |
| 2. | Explain system | Patient responds. |
| 3. | Tell patient to turn on power. | Patient attaches electrodes. |
| 4. | Record patient name, address, etc. | Patient gives data. |
| 5. | Record data, choose | |

TABLE II-continued

Typical Sequence for Monitoring Call
Codes to be used with
Touch-Tone Telephone at Center

| Step | Center Operation | Patient Operation |
|---|---|---|
| | 5a, 5b or 5c | |
| | 5a. No pulse data desired, depress 1!-6 | ECG is recorded. |
| | 5b. Only pulse rate and ECG desired, press 1!-5 | ECG and time of pulse occurrence recorded. |
| | 5c. Pulse duration and ECG desired, press 1!-4 | ECG and pulse width recorded. |
| 6. | (At any time) talk to patient, depress 1!-7. Tell patient to apply magnet. | Patient is alerted, talks to operator. Patient applies magnet. |
| 7. | Record data, choose 7a or 7b | Pacemaker patient only |
| | 7a. Only pulse rate and ECG desired, press 1-5! | ECG and time of pulse occurrence recorded. |
| | 7b. Pulse duration and ECG desired, press 1!-4 | ECG and pulse width recorded. |
| 8. | (At any time) talk to patient, depress 1-7! | Patient is alerted, talks to operator. Tell patient to apply magnet. |
| 9. | Tell patient test is over | Patient removes electrodes, etc. |
| 10. | Depress 1!-0 | Test over, transmitter turned off. |

NOTE:
The symbol "1!" indicates that the "1" key is to be depressed for at least 3 seconds.

A particular embodiment of the invention uses the following specifications:

| Electrical | |
|---|---|
| Battery Type: | 9 v transistor |
| Current: | <15 mA, |
| Low battery indicator: | Yes |
| Bandwidth (−3 db): | .5 to 40 hz |
| Common Mode Rejection Ratio: | >60 db |
| Input Impedance: | 2 Megohms |
| Modulation characteristics | |
| Method: | Frequency Modulation |
| Center frequency, ECG: | 1500 hz, ±7% |
| Range of ECG signal: | ±5 mv |
| Frequency deviation: | 50 hz/mv |
| Center frequency, Pacemaker signal: | 2200 hz |
| Length increased by: | 33 times |
| Minimum pacemaker pulse sensed: | .8 mv |
| Range of durations measured: | .1 to 2.5 msec |
| Duration accuracy: | ±20 usec |

An alternative embodiment is to use a cellular telephone in place of modified telephone set 10c in FIG. 3, i.e., to couple monitoring part 10a and isolation stage 10b of FIG. 3 to a cellular telephone represented by part 10c, in which case telephone control 58 will comprise the RF receiving and transmitting circuitry of a cellular telephone.

Figure 6:
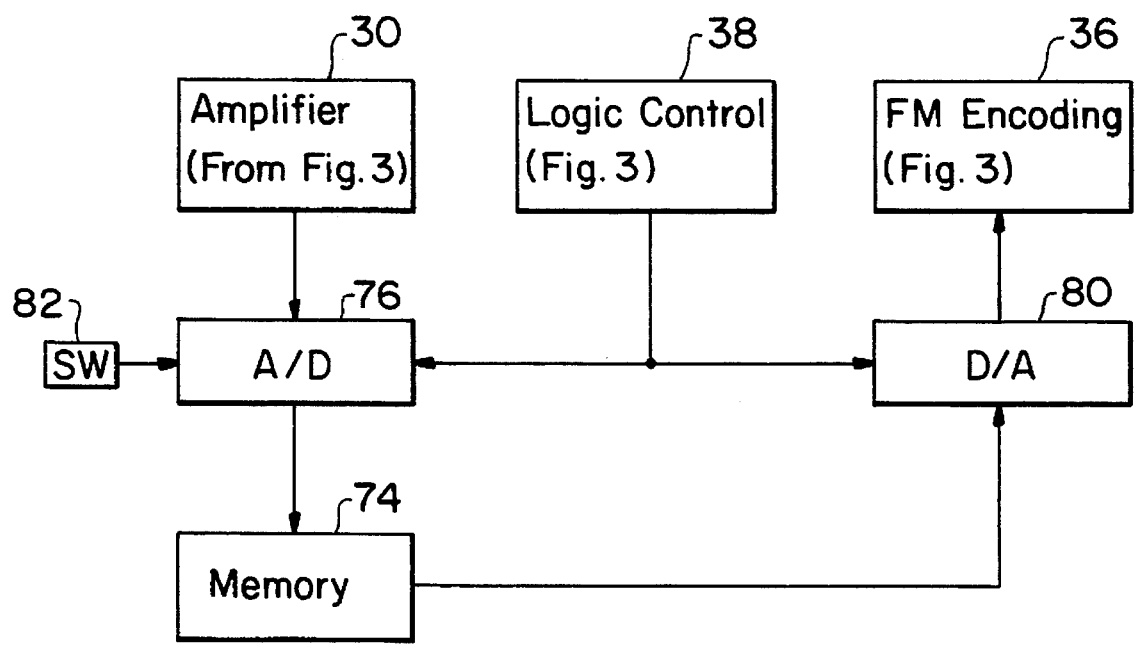
FIG. 6 illustrates a modification of FIG. 3 for implementing yet another alternative embodiment which included event recording functions.

Yet another alternative embodiment includes event recorder functions in the home instrument in addition to the functions described above. Referring to FIGS. 3 and 6, monitoring part 10a is modified by the addition of circuitry including a memory 74 such a RAM memory capable of storing ECG events in digital form. An A/D converter 76 when enabled convert the analog output of amplifier 28 to digital form for storage in memory 74, while a D/A converter 80 when enabled converts the digital information stored in memory 74 to analog form to delivery to FM encoder 36. A/D converter 76 is enabled by a local control signal from either one of a manually operated switch 82 and a respective local command from logic control 38, while D/A converter 80 is enabled by a respective local command from logic control 38. In operation, the patient attaches ECG electrodes such as 20 and 22 as earlier discussed and, at a suitable time, operates switch 50a to power up the local instrument and switch 82 to turn on the recording function. Alternatively, the patient after connecting the ECG electrodes establishes a telephone connection with central station 26, or central station 26 calls the patient to establish the telephone connection and to ask the patient to connect the ECG electrodes and power local instrument 10. Then, the person at central station 26 enters a command through the dialing keys or otherwise, and central station 26 translates the command into a respective DTMF signal which is transmitted to local instrument 10 via the telephone. Local instrument 10 decodes the DTMF signal at decoder 64 into a local command for logic control 38 to turn on the event recording function through a command to A/D converter 76. Another similarly generated and transmitted DTMF signal is locally decoded to turn off A/D converter 76 and, when appropriate, to turn on D/A converter 80 to deliver the stored information to FM encoder 36 for transmission to central station 26. The incorporated event recording function can be used in any of the embodiments discussed above, i.e., with a local telephone set as in FIG. 1, with a portable telephone set as in FIG. 4, with an acoustically coupled unit as in FIG. 5, or with in a cellular phone as earlier discussed in connection with FIG. 3.

We claim:

1. A cardiac patient follow up system comprising a local instrument having ECG lead inputs for connection to ECG electrodes coupled with a patient and further having telephone line inputs for connection with a central instrument through a telephone network utilizing dual tone multifrequency signals for dialing, said local instrument comprising:

a local telephone set for establishing a two-way telephone connection with said central instrument through a telephone line and telephone network, said local telephone set having a telephone circuit including a speaker for converting a voice signal received over said telephone line to a sound signal and a microphone converting a sound signal received at the microphone into a signal for transmission over said telephone line and network; and a local dual tone multifrequency decoder responsive to dual tone multifrequency signals received over said telephone line to generate respective local command signals;

a patient monitoring portion coupled to said telephone set, said patient monitoring portion including:

an amplifier coupled with said inputs for ECG leads to amplify signals received thereat;

an ECG filter and a pulse filter each coupled with the amplifier to receive signals amplified thereby, said ECG filter comprising circuitry tending to pass ECG signals while suppressing pulse signals corresponding to cardiac pacemaker pulses, and said pulse filter comprising circuitry tending to pass pulse signals corresponding to cardiac pacemaker pulses while suppressing ECG signals;

a pulse detector coupled with said pulse filter to detect leading and trailing edges of pulses passed thereby and to generate in response relatively short pulses signifying said leading and trailing edges;

a pulse width encoder coupled with said pulse detector and, when enabled by a respective local command, responding to each pair of said short pulses corresponding to a pacemaker pulse to generate a respective pulse width encoded signal;

a fixed pulse encoder coupled with said pulse detector and, when enabled by a respective local command, responding to each pair of said short pulses corresponding to a pacemaker pulse to generate a respective fixed width pulse;

an FM encoder coupled with said pulse width encoder and said fixed pulse encoder and, when enabled by a respective local command, receiving said pulse width encoded signal and said fixed width pulse therefrom and encoding said pulse width encoded signal and said fixed width pulse into an FM signal having a specified center frequency and deviations therefrom corresponding to parameters of said pulse width encoded signal and said fixed width pulse for transmission over said telephone line and network to said central instrument;

a patient alert indicator displaying at least one message for a patient using said local instrument;

a logic control circuit coupled with said local dual tone multifrequency decoder and responsive to said local command signals therefrom to generate respective local commands for selectively enabling said FM encoder, pulse encoder, pulse width encoder, and patient alert indicator; and an isolation stage connecting said FM encoder and said logic control circuit with said telephone circuit to pass information therebetween while suppressing electrical interaction therebetween.

2. A system as in claim 1 in which said local telephone set is packaged in a base enclosure and a handset connected therewith with a cord, and said local dual tone multifrequency encoder, amplifier, filter, pulse detector, encoders and logic control are integrally packaged in said base enclosure.

3. A system as in claim 1 in which said local telephone set comprises a portable telephone set having a base unit and an internally powered handset communicating with each other via a wireless connection, and at least said amplifier, filter and pulse detector being housed in said handset, wherein said wireless connection serves as said isolation stage.

4. A system as in claim 1 in which said local telephone set comprises a handset housing said speaker and microphone, and said isolation stage comprises an acoustic coupler for coupling said speaker and microphone with said FM encoder and logic control circuit.

5. A system as in claim 1 in which said local telephone set comprises a cellular telephone.

6. A cardiac patient follow up method comprising the steps of:

establishing a two-way telephone connection between a local instrument and a central station through a telephone line and telephone network using dual tone multifrequency signals for dialing;

decoding at the local instrument dual tone multifrequency signals received over said telephone line frequencies to generate respective local command signals;

coupling ECG electrodes to said local instrument and amplifying signals received from said electrodes to generate amplified signals;

ECG filtering the amplified signals to pass ECG signals while suppressing pulse signals corresponding to cardiac pacemaker pulses, and pulse filtering the amplified signals to pass pulse signals corresponding to cardiac pacemaker pulses while suppressing ECG signals;

detecting leading and trailing edges of pulses passed by said pulse filtering and generating, in response to detected edges, relatively short pulses signifying said detected edges;

pulse width encoding pairs of said short pulses corresponding to pacemaker pulses to generate respective pulse width encoded signals;

fixed pulse encoding pairs of said short pulses corresponding to pacemaker pulses to generate respective fixed width pulses;

FM encoding selected pulse width encoded signals and fixed width pulses into an FM signal having a specified center frequency and deviations therefrom for transmission over said telephone line and network to said central station; and generating local commands in response to said decoding of dual tone multifrequency signals received over the telephone line, and controlling operational parameters of said pulse width encoding, fixed pulse encoding, and FM encoding in accordance with said local commands.

7. A system comprising:

a central instrument coupled to a telephone switching office network;

a local instrument having a decoder for decoding dual tone multifrequency signals received over a telephone network after a two-way telephone connection has been established between the local instrument and the central instrument through the telephone switching office network, said decoder generating selected local commands in response to said dual tone multifrequency signals;

a patient monitoring circuit having inputs for receiving physiological signals from ECG electrodes coupled with a cardiac patient, a plurality of signal processing circuits coupled to said inputs, a logic control circuit responsive to said local commands to selectively enable and disable selected ones of said signal processing circuits to thereby apply selected processing operations to physiological signals received at said inputs and to provide respective output signals; and an encoder selectively coupled to said signal processing circuits to encode output signals therefrom for transmission to said central instruments through said local instrument and said telephone network.

8. A system as in claim 7 in which said decoder is responsive to said dual tone multifrequency signals to generate at least four different local commands.

9. A system as in claim 7 in which said decoder comprises a local dual tone multifrequency decoder responsive to the dual tone multifrequency signals for dialing.

10. A system as in claim 7 in which said plurality of signal processing circuits comprise an ECG processing path for extracting ECG signals from said signals applied to said inputs, a pulse width encoding path for converting pulses received at said inputs as a result of pacemaker pulses into transmission pulses which are wider by at least an order of magnitude, and a fixed pulse encoding path for converting pulses received at said inputs as a result of pacemaker pulses into pulses of fixed width, and in which said logic control circuit comprises circuits for selectively enabling and disabling said paths to generate respective output signals for encoding by said encoder.

11. A system as in claim 7 in which said encoder comprises an FM encoder carrying out FM encoding.

12. A system as in claim 7 including an event recorder coupled with said inputs and said logic control circuit and responsive to respective local commands to record signals applied to said inputs and to supply the recorded signals for transmission to the central instrument via said encoder.

13. A system as in claim 12 in which said event recorder comprises a digital memory for recording signals containing information regarding cardiac events in digital form.

14. A method of remotely monitoring a cardiac patient comprising the steps of:

decoding, at a local instrument, dual tone multifrequency signals received over a telephone network after a two-way telephone connection has been established between the local instrument and a central instrument through a telephone switching office network using dual tone multifrequency dialing;

generating selected local commands corresponding to said dual tone multifrequency signals in response to said decoding;

receiving physiological signals from ECG electrodes coupled with a cardiac patient and processing said signals;

selectively enabling and disabling selected signal processing paths for processing said signals to thereby apply selected processing operations to physiological signals received at said inputs and to provide respective output signals; and selectively coupling an encoder to said signal processing paths to encode output signals therefrom for transmission to said central instrument through said local instrument and said telephone network.

* * * * *